(12) United States Patent
McGavern et al.

(10) Patent No.: US 9,308,163 B2
(45) Date of Patent: Apr. 12, 2016

(54) METHODS OF TREATING AND PREVENTING DISEASES AND DISORDERS OF THE CENTRAL NERVOUS SYSTEM

(71) Applicant: The United States of America, as represented by the Secretary, Department of Health and Human, Bethesda, MD (US)

(72) Inventors: Dorian B. McGavern, Gaithersburg, MD (US); Theodore Roth, Birmingham, AL (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/377,348

(22) PCT Filed: Feb. 5, 2013

(86) PCT No.: PCT/US2013/024741
§ 371 (c)(1),
(2) Date: Aug. 7, 2014

(87) PCT Pub. No.: WO2013/122778
PCT Pub. Date: Aug. 22, 2013

(65) Prior Publication Data
US 2015/0011626 A1    Jan. 8, 2015

Related U.S. Application Data

(60) Provisional application No. 61/599,107, filed on Feb. 15, 2012.

(51) Int. Cl.
| | | |
|---|---|---|
| *A61K 31/64* | (2006.01) | |
| *A61K 31/235* | (2006.01) | |
| *A61K 31/7076* | (2006.01) | |
| *A61K 9/00* | (2006.01) | |
| *A61K 31/375* | (2006.01) | |
| *A61K 38/06* | (2006.01) | |
| *A61K 31/05* | (2006.01) | |
| *A61K 31/22* | (2006.01) | |
| *A61K 31/26* | (2006.01) | |
| *A61K 31/355* | (2006.01) | |
| *A61K 31/385* | (2006.01) | |
| *A61K 31/522* | (2006.01) | |

(52) U.S. Cl.
CPC .............. *A61K 9/0085* (2013.01); *A61K 31/05* (2013.01); *A61K 31/22* (2013.01); *A61K 31/235* (2013.01); *A61K 31/26* (2013.01); *A61K 31/355* (2013.01); *A61K 31/375* (2013.01); *A61K 31/385* (2013.01); *A61K 31/522* (2013.01); *A61K 31/64* (2013.01); *A61K 31/7076* (2013.01); *A61K 38/063* (2013.01)

(58) Field of Classification Search
None
See application file for complete search history.

(56) References Cited

U.S. PATENT DOCUMENTS

| | | |
|---|---|---|
| 7,923,448 B2 | 4/2011 | Nedergaard et al. |
| 7,981,901 B2 | 7/2011 | Frome |
| 2005/0143344 A1 | 6/2005 | Zeldis et al. |
| 2006/0013802 A1 | 1/2006 | Shafer |
| 2007/0259920 A1 | 11/2007 | Carroll et al. |
| 2010/0080797 A1 | 4/2010 | Yeomans et al. |
| 2010/0113380 A1 | 5/2010 | Bratcher et al. |
| 2010/0210654 A1 | 8/2010 | Müller et al. |
| 2010/0256123 A1 | 10/2010 | Sakuma et al. |
| 2011/0092703 A1 | 4/2011 | Sakuma et al. |
| 2011/0176994 A1 | 7/2011 | Pratt et al. |

FOREIGN PATENT DOCUMENTS

| | | |
|---|---|---|
| WO | WO 01/10455 A1 | 2/2001 |
| WO | WO 2006/128735 A1 | 12/2006 |
| WO | WO 2011/047091 A1 | 4/2011 |

OTHER PUBLICATIONS (http://www.nlm.nih.gov/medlineplus/neurologicdiseases.html) (accessed Feb. 7, 2015).*
National Institute of Neurological Disorders and Stroke (NINDS) (accessed Feb. 7, 2015).*
autism (NINDS Autism Information page, accessed Feb. 7, 2015).*
ALS (NINDS ALS information page, accessed Feb. 7, 2015).*
Khan et al. (Journal of Neuroinflammation 2009, 6:32).*
Pathirana et al. (Indian J Pharm Sci. May-Jun. 2009;71(3):264-269).*

(Continued)

*Primary Examiner* — James H Alstrum Acevedo
*Assistant Examiner* — Tara Martinez
(74) *Attorney, Agent, or Firm* — Leydig, Voit & Mayer, Ltd.

(57) ABSTRACT

Disclosed is a method of treating or preventing a disease or disorder of the central nervous system (CNS) in a patient comprising administering transcranially, for example, directly to the skull, an effective amount of an anti-inflammatory agent to the patient. Examples of the anti-inflammatory agent include glutathione and inhibitors of purinergic receptors such as $P2X_4$, $P2X_7$, $P2Y_6$, and $P2Y_{12}$ receptors. Examples of disease or disorder of the CNS include brain injury, particularly traumatic brain injury, inflammation, infection, degeneration of brain cells, stroke, brain edema, tumor, Alzheimer's disease, Parkinson's disease, and multiple sclerosis. Also disclosed is a kit comprising at least one anti-inflammatory agent and printed materials containing instructions for transcranially administering the anti-inflammatory agent to the patient having a disease or disorder of the CNS, disorder of the CNS.

7 Claims, 10 Drawing Sheets

(56) References Cited

OTHER PUBLICATIONS

GlutaSource info (Traumatic Brain Injury and Glutathione Therapies, Oct. 24, 2011).*
Extended European Search Report, Application No. 13748662.7, dated Jun. 9, 2015.
Bibolini et al., "Inhibitory role of diazepam on autoimmune inflammation in rats with experimental autoimmune encephalomyelitis" *Neuroscience* 199, 421-428 (2011).
Miura et al., "Intraventricular ascorbic acid administration decreases hypoxic-ischemic brain injury in newborn rats," *Brain Research* 1095(1), 159-166 (2006).
Pathirana et al., "Brain targeted transcranial route of drug delivery of diazepam," *Indian Journal of Pharmaceutical Sciences* 68(4), 493-496 (2006).
Pathirana et al., "Brain targeted transcranial administration of diazepam and shortening of sleep latency in healthy human volunteers," *Indian Journal of Pharmaceutical Sciences* 73(5), 497-503 (2011).
Sarnowska et al., "Diazepam neuroprotection in excitotoxic and oxidative stress involves a mitochondrial mechanism additional to the GABAAR and hypothermic effects," *Neurochemistry International* 55(1-3), 164-173 (2009).
Burnstock et al., "Purinergic signalling and disorders of the central nervous system," *Nat. Rev. Drug Discov.*, 7 (7), 575-590 (2008).
International Search Report, Application No. PCT/US2013/024741, dated May 30, 2013.
International Preliminary Report on Patentability, Application No. PCT/US2013/024741, dated Aug. 19, 2014.
Khan et al., "Administration of S-nitrosoglutathione after traumatic brain injury protects the neurovascular unit and reduces secondary injury in a rat model of controlled cortical impact," *J. Neuroinflammation*, 6 (32) (2009) (12 pages).
Pathirana et al., "Transcranial Route of Brain Targeted Delivery of Methadone in Oil," *Indian J. Pharm. Sci.*, 71 (3), 264-269 (2009).
Rajadhyaksha et al., "Current Advances in Delivery of Biotherapeutics Across the Blood-Brain Barrier," *Curr. Drug Disc. Tech.*, 8, 87-101 (2011).
Tuttolomondo et al., "Inflammation as a therapeutic target in acute ischemic stroke treatment," *Curr. Top Med. Chem.*, 9 (14), 1240-1260 (2009).
Written Opinion of the International Searching Authority, Application No. PCT/US2013/024741, dated May 29, 2013.
Zhong et al., "Biomaterials for the central nervous system," *J. R. Soc. Interface*, 5, 957-975 (2008).

* cited by examiner

US 9,308,163 B2

METHODS OF TREATING AND PREVENTING DISEASES AND DISORDERS OF THE CENTRAL NERVOUS SYSTEM

CROSS-REFERENCE TO A RELATED APPLICATION

This application is the U.S. national phase of International Patent Application No. PCT/US2013/024741, filed Feb. 5, 2013, which claims the benefit of U.S. Provisional Patent Application No. 61/599,107, filed Feb. 15, 2012, the disclosures of which are incorporated herein by reference.

BACKGROUND OF THE INVENTION

The central nervous system (CNS) of an animal, for example, human, contains several important receptor systems such as the glutamate, acetylcholine, $GABA_A$, and NMDA receptor systems, and injury to the CNS as well as other diseases and disorders of the CNS could be quite serious including threat to life. For example, following a traumatic injury to the CNS, a cascade of physiological events can lead to neuronal loss, including, for example, an inflammatory immune response and excitotoxicity resulting from the initial impact of one or more of the above receptor systems. In addition, traumatic CNS injury can be accompanied by brain edema that enhances the cascade of injury and can lead to further secondary cell death and increased mortality of the animal.

An example of the CNS injury is traumatic brain injury (TBI) to the brain, which is a head injury caused by trauma to the brain. Symptoms of TBI include headache, confusion, dizziness, blurred vision, changes in mood, impairment of cognitive function such as memory, learning, and attention, nausea, convulsions or seizures, slurring of speech, numbness of extremities, and loss of coordination. While some symptoms appear immediately, others do not appear until days, months or even years after the TBI event. TBI is a major cause of preventable death and morbidity, and disability following injury in war zones, in sports and recreation, and general population falls and accidents. Secondary injury occurring hours and days after the head trauma occurs as a result of ischemia, blood brain barrier leakage and inflammatory/oxidative stress.

Attempts to treat diseases and disorders of the CNS, particularly TBI, that target neuroprotection following TBI have proven to be of little efficacy. The blood brain barrier (BBB) has been a cause of many drugs' ineffective translation from "promising" to "failure" in the treatment or prevention of various brain injury and other CNS disease or disorders. Much resources have been spent on developing drugs which when administered systemically have proven to be ineffective. This failure is believed to be due to the blockage of the drug by the BBB from reaching the CNS, wherein the blockage leads to inadequate concentration of the drug in the CNS.

The foregoing shows that there is an unmet need for a treatment modality that can effectively administer a drug to the CNS, thereby treating and/or preventing a disease or disorder of the CNS.

BRIEF SUMMARY OF THE INVENTION

The foregoing need has been fulfilled by the invention. Accordingly, the invention provides a method of treating or preventing a disease or disorder of the central nervous system (CNS) in a patient comprising administering transcranially an effective amount of reactive oxygen scavenger (ROS) or an anti-inflammatory agent to the patient. The invention further provides a method of inhibiting, reducing, or eliminating the formation of reactive microglia in a patient suffering from a traumatic brain injury comprising administering transcranially an effective amount of an anti-inflammatory agent to the patient.

The invention also provides a method of inhibiting, reducing, or eliminating the recruitment of neutrophils and/or monocytes in a patient suffering from a traumatic brain injury comprising administering transcranially an effective amount of an anti-inflammatory agent to the patient. The invention further provides a method of reducing the number of dead cells in the brain parenchyma or meninges in a patient suffering from a traumatic brain injury comprising administering transcranially an effective amount of an anti-inflammatory agent to the patient. The invention also provides a kit comprising at least one anti-inflammatory agent and printed materials containing instructions for transcranially administering the anti-inflammatory agent to the patient having a disease or disorder of the central nervous system (CNS).

The present invention provides methods wherein therapeutic agents penetrate the skull and pass into the cerebrospinal fluid. The approach of the present invention allows the therapeutic agents bypass the blood brain barrier (BBB) and the agents rapidly reach the injured or inflamed areas of the CNS. The invention provides methods wherein a high local concentration of the therapeutic agent is quickly established at the site of the CNS injury.

In embodiments of the invention, the reactive oxygen scavengers rapidly eliminate free radicals generated as a result of the CNS injury. In embodiments of the invention, purinergic antagonists block the damage sensing ability of the purinergic receptors, thereby stopping the innate immune cells to activate the brain resident microglia or prevent the arrival of peripherally-derived neutrophils, which are the two innate inflammatory cells. The invention also provides a pharmaceutical composition for transcranially treating or preventing a disease or disorder of the central nervous system (CNS) comprising an anti-inflammatory agent as the main ingredient. The pharmaceutical composition is adapted for or is suitable for transcranial administration.

BRIEF DESCRIPTION OF THE SEVERAL VIEWS OF THE DRAWING(S)

FIG. 1 depicts the number of dead cells in the meninges and parenchyma of mice as a function of time after meningeal compression injury.

FIG. 2 illustrates the distribution of fluorescent probes in the brain as a function of their molecular weight after transcranial administration of the probes to intact (non-thinned) skull of mice. White indicates that the probes were found in the subarachnoid space of the brain and black indicates they were not present therein. Gray indicates that the probe was not tested at that time.

FIG. 3 depicts the percentage of microglia with jellyfish morphology found after administration of purinergic receptor antagonists to the skull of mice prior to inducing meningeal compression injury. MRS2578 (500 µm; $P2Y_6$ antagonist); MeSAMP (10 mM; $P2Y_{12}$ antagonist); TNP-ATP hydrate (25 mM; $P2X_4$ antagonist), and oxidized ATP (10 mM; $P2X_7$ antagonist).

DETAILED DESCRIPTION OF THE INVENTION

Figure 1:
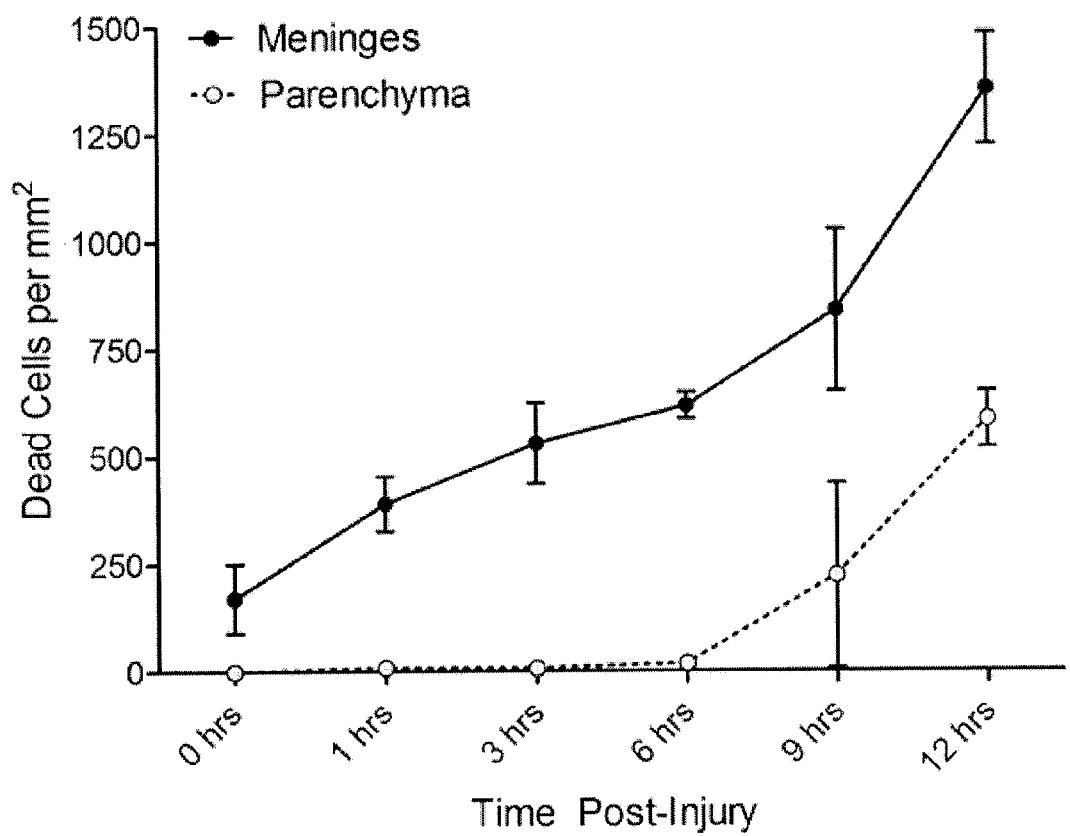

The present invention relies, at least in part, on the ability of the compounds of the invention to pass through the skull bone taking advantage of the porous nature of the skull bone. All three layers of the skull bone, the upper cortical, the cancellous, and the lower cortical layers are porous to varying degrees. The cancellous bone is known to be highly porous. As a result, compounds can be applied to the skull bone, and they can reach the CNS. In accordance with the present invention, the compounds can diffuse directly through the skull bone itself, especially if a compound is applied directly to or injected into the skull bone. The skull of a mammal has anatomical features that allow delivery of therapeutic agents to the CNS effectively and rapidly.

In an embodiment, when a compound of the invention is applied to the scalp, the compound may access the emissary veins. The emissary veins draining blood from extracranial sites into the intracranial sinuses pierce a series of foramina present in the cranial bones. Scalp veins communicate with the sinuses of the brain via emissary veins. There are thirteen emissary veins connecting extracranial sites of the human head with intracranial sinuses. Seven major sinuses within the skull are inter-connected by a number of anatomizing veins, which finally drain intracranially into jugular veins giving ample scope for the diffusion of the drug molecules into the nerve tissue of the brain.

Accordingly, in accordance with an embodiment, the invention provides a method of treating or preventing a disease or disorder of the central nervous system (CNS) in a patient comprising administering transcranially an effective amount of a reactive oxygen scavenger or an anti-inflammatory agent to the patient. The disease or disorder of the CNS can be any suitable disease or disorder, for example, those selected from the group consisting of brain injury, inflammation, infection, degeneration of brain cells, stroke, brain edema, tumor, Alzheimer's disease, Parkinson's disease, and multiple sclerosis. In a particular embodiment, the disease or disorder of the CNS is brain injury, and more particularly traumatic brain injury (TBI).

In accordance with another embodiment, the invention provides a method of inhibiting, reducing, or eliminating the formation of reactive microglia in a patient suffering from a traumatic brain injury comprising administering transcranially an effective amount of an anti-inflammatory agent to the patient. In a further embodiment, the invention provides a method of inhibiting, reducing, or eliminating the recruitment of neutrophils and/or monocytes in a patient suffering from a traumatic brain injury comprising administering transcranially an effective amount of an anti-inflammatory agent to the patient. In yet another embodiment, the invention provides a method of reducing the number of dead cells in the brain parenchyma or meninges in a patient suffering from a traumatic brain injury comprising administering transcranially an effective amount of an anti-inflammatory agent to the patient.

The CNS disease or disorder, e.g., TBI, can arise from activity associated with boxing, football, soccer, hockey, armed conflict, or brain surgery.

The various changes occurring in the CNS, particularly brain, which has been injured or a CNS, particularly brain, undergoing treatment can be assessed by the imaging techniques described in Example 1.

Additionally, the presence of traumatic brain injury in a patient can be assessed by standard techniques used by a physician of skill in the art. These include, among others, Glasgow Coma Scale, which is a 15-point test that helps assess the severity of a brain injury by checking patient's ability to follow directions, to blink the eyes or to move extremities; brain imaging techniques, including computer assisted tomography (CAT) scans, which allow visualization of fractures and evidence of bleeding in the brain (hemorrhage), large blood clots (hematomas), bruised brain tissue (contusions), and brain tissue swelling. In embodiments, the brain imaging technique used can be magnetic resonance imaging (MRI), including Susceptibility Weighted Images (SWI), a sensitive method for detecting small hemorrhages in the brain, and Diffusion tensor imaging (DTI), which consists of a minimum of six scans with diffusion gradients placed in an orthogonal manner. In some embodiments, traumatic brain injury can be assessed by measuring intracranial pressure, which can occur by swelling of the brain.

Since neurobehavioral, particularly cognitive related, problems are a major effect of traumatic brain injury, various methods used to assess cognitive function can be used. Such assessments include, among others, the following: Clinical Dementia Rating Scale (CDR), a dementia staging instrument that classifies cognitive impairment along a continuum from normal aging to mild cognitive impairment to all stages of dementia severity; Folstein Mini-Mental State Exam (MMSE), which is commonly used to measure of orientation and gross cognitive functioning used by physicians and healthcare providers to screen for cognitive decline; and Alzheimer's Disease Assessment Scale-Cognitive (ADAS-C), a test commonly used in detection of dementia and mild cognitive impairment.

Additional methods for assessing cognitive impairment from traumatic brain injury can include, among others, various neuropsychological test, such as the following: Wechsler Test of Adult Reading (WTAR), which is a measure of word pronunciation and is a reliable predictor of pre-morbid general intellectual function; Wechsler Adult Intelligence Scale-3 (WAIS-3)-Kaufman tetrad short form, which is used to measure general intellectual functioning; Repeatable Battery for the Assessment of Neuropsychological Status (RBANS), a comprehensive but relatively rapid, standardized measure of neurocognitive functioning in multiple domains, including memory, attention, language, and visuospatial/constructional functions; Trailmaking Test Part A (Trails A), a widely-used measure of cognitive processing and visuomotor speed, and with Part B, also previously employed in studies of mild cognitive impairment (MCI); Trailmaking Test Part B (Trails B), a more complex measure of cognitive processing with executive demands related to mental flexibility and working memory; Controlled Oral Word Association Test (COWAT), a well-known measure of phonemically-controlled verbal fluency, sensitive to cognitive slowing and impairments of executive functioning and routinely employed in dementia assessment and MCI studies; Boston Naming Test (BNT), a visual confrontation naming measure utilized to detect anomia or word-finding difficulties, which are common hallmarks of cognitive decline in elderly populations with mild cognitive impairment or early dementia; Automated Neuropsychological Assessment Metrics (ANAM), a computerized test designed to assess several cognitive domains known to be sensitive to change following concussion, including attention and concentration, reaction time, working memory, new learning and memory, and speed of information processing; and SF-36, which measures eight domains of health, including, physical functioning, role limitations due to physical health, bodily pain, general health perceptions, vitality, social functioning, role limitations due to emotional problems, and mental health.

The various processes that undergo in the CNS after an injury can be quite complex. For example, in TBI, particularly in meningeal compression injury, the meningeal macrophages undergo rapid necrosis, releasing their contents into the subarachnoid space. This mediates a breach in the glial limitans, which in turn, triggers transformation of the underlying parenchymal microglia into massive phagocytic machines with a jellyfish-like morphology. These microglia migrate to the compromised glial limitans and appear to form a phagocytic barrier between the meninges and brain parenchyma. The phagocytic microglia are always associated with areas of barrier compromise despite the continued survival of astrocytes comprising glial limitans. The microglial response to meningeal compression is immediate and is followed shortly thereafter by swarms of neutrophils that invade the injury site.

The present invention further provides a kit or package comprising at least one anti-inflammatory agent and printed materials containing instructions for transcranially administering an anti-inflammatory agent to the patient having a disease or disorder of the central nervous system (CNS). The kit or package can further include a device for administering the anti-inflammatory agent to the head, scalp, or skull bone of the patient. The kit or package can contain one dosage form, or more than one dosage form, i.e., multiple dosage forms. If multiple dosage forms are present in the kit or package, the multiple dosage forms can be optionally arranged for sequential administration. The kit or package can contain dosage forms of a sufficient number for 1, 2, 3, 4, or more weeks, or months, of daily or weekly administration of the anti-inflammatory agent.

The kit or package can optionally include instructions with dosage forms. Such instructions can be in a form prescribed by a government agency regulating manufacture, use or sale of pharmaceutical products, which notice reflects approval by the agency of the manufacture, use or sale for human administration to treat the disease or disorder. The instructions can be in any form that conveys information on the use of the dosage forms in the kit or package according to the methods described herein. By way of example, the instructions can be in the form of a printed matter, or in the form of a pre-recorded media device.

In any of the above embodiments, the brain injury involves meningeal compression injury.

In any of the above embodiments, the ROS or anti-inflammatory agent is selected from the group consisting of antioxidants, purinergic receptor inhibitors, and connexin hemichannel inhibitors.

The ROS or anti-inflammatory agent can have any suitable molecular weight, preferably a low molecular weight compound. For example, the molecular weight, particularly the number average molecular weight, of the anti-inflammatory agent can be up to about 40,000 Daltons, particularly from about 300 to about 10,000 Daltons, and more particularly from about 300 to about 1000 Daltons. In an embodiment, the anti-inflammatory agent has a molecular weight, e.g., number average molecular weight, of about 600 to 1000 Daltons. In another embodiment, the anti-inflammatory agent has a molecular weight, e.g., number average molecular weight, of about 400 to 500 Daltons.

In embodiments, the ROS or anti-inflammatory agent passes through the skull by a diffusion mechanism. Thus, smaller molecular weight agents reach the desired site of action more quickly than larger molecular weight agents.

In a particular embodiment, the ROS or anti-inflammatory agent is an antioxidant, for example, an antioxidant selected from the group consisting of glutathione, ascorbic acid, lipoic acid, uric acid, carotenes, α-tocopherol, ubiquinols, and combinations thereof, and more particularly, glutathione.

In an embodiment, the ROS or anti-inflammatory agent or antioxidant is not docosahexaenoic acid or eicosapentaenoic acid or salts or esters thereof.

In accordance with an embodiment, the ROS or anti-inflammatory agent is a purinergic receptor inhibitor, for example, a P2X or a P2Y receptor inhibitor. Examples of such inhibitors include $P2X_4$ receptor inhibitors, $P2X_7$ receptor inhibitors, $P2Y_6$ receptor inhibitors, and $P2Y_{12}$ receptor inhibitors.

In a particular embodiment, the inhibitor is a $P2X_4$ receptor inhibitor. Any suitable $P2X_4$ receptor inhibitor can be used. For example, trinitrophenyl-ATP hydrate can be used as a $P2X_4$ receptor inhibitor.

Examples of other $P2X_4$ receptor inhibitors include 1,4-diazepin-2-one derivatives disclosed in WO 2004/085440 A1 and US 2010/0256123 A1, piperazine derivatives disclosed in WO 2005/037803 A1, WO 2004/089915 A1, and US 2011/0092703 A1, and tricyclic compounds disclosed in WO 2007/072974 A1, WO 2007/074940 A1, and WO 2008/023847 A1. For example, the $P2X_4$ receptor inhibitor can be, as disclosed in WO 2004/085440 A1, of formula (A) shown below:

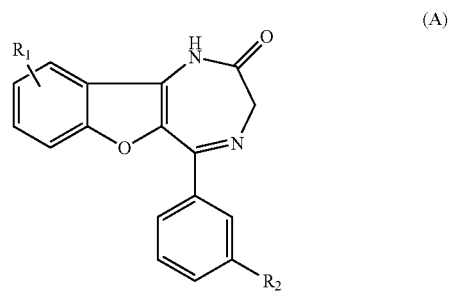

(A)

in which $R_1$ is halogen and $R_2$ is hydrogen, halogen, nitro, cyano, C(O)—$OR_3$, C(O)—$NR_4R_5$, $SO_2$—$OR_3$, or $SO_2$—$NR_4R_6$, or $R_1$ is hydrogen and $R_2$ is halogen, nitro, cyano, C(O)—$OR_3$, C(O)—$NR_4R_5$, $SO_2$—$OR_3$ or $SO_2$—$NR_4R_6$, wherein $R_3$, $R_4$, and $R_5$ are hydrogen or alkyl.

In a particular embodiment, the inhibitor is a $P2X_7$ receptor inhibitor. Any suitable $P2X_7$ receptor inhibitor can be used. For example, oxidized ATP (o-ATP) can be used as a $P2X_7$ receptor inhibitor, which is a ribose ring-opened dialdehyde analog of ATP. The oxidation of ATP can be carried out by a periodate.

Examples of other $P2X_7$ receptor inhibitors include the pyrazole derivatives disclosed in US 2007/0259920 A1, the amino-tetrazole derivatives disclosed in WO 2005/111,003 A1, as well as 1-[N,O-bis(5-isoquinolinesulfonyl)-N-methyl-L-tyrosyl]-4-phenylpiperazine, hexamethylene amiloride, and brilliant blue G. For example, a $P2X_7$ receptor inhibitor, as disclosed in US 2007/0259920 A1, can be a compound of formula (I):

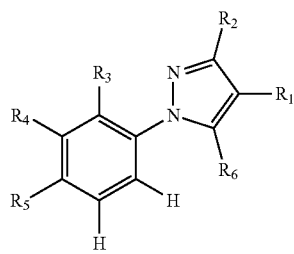

(I)

or a pharmaceutically acceptable salt, prodrug, salt of prodrug, or a combination thereof,
wherein
$R_1$ is hydrogen or —CN, and $R_2$ is hydrogen, or
$R_1$ and $R_2$ together with the carbon atoms to which they are attached, form a monocyclic saturated ring consisting of 5, 6 or 7 carbon atoms and one of the carbon atoms of the ring is optionally replaced by a heteroatom selected from the group consisting of S, N, NH, O, SO and $SO_2$; and said ring is optionally substituted with 1 or 2 substituents selected from the group consisting of alkyl, halogen, haloalkyl, —C(O)alkyl, and —S(O)$_2$alkyl;
$R_3$ is halogen, —CN, haloalkyl, alkoxy or haloalkoxy;
$R_4$ is alkyl, halogen, —CN, haloalkyl, alkoxy or haloalkoxy;
$R_5$ is hydrogen, alkyl, halogen, —CN, haloalkyl, alkoxy or haloalkoxy;
$R_6$ is —N(H)—W, or —N(H)—C($R_x$)(H)—$W_1$; wherein
$R_x$ is hydrogen, alkyl or haloalkyl,
W is

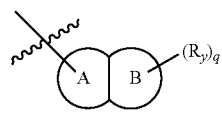

wherein
A is a five or six membered monocyclic ring selected from the group consisting of cycloalkyl and heterocycle and is optionally substituted with 1, 2, or 3 substituents selected from the group consisting of alkyl, halo and haloalkyl;
B is phenyl or monocyclic heteroaryl, optionally substituted with 1, 2 or 3 substituents selected from the group consisting of halo, alkyl, —CN, —$OR_A$, —$SR_A$, —N($R_A$)($R_B$) and haloalkyl;

q is 0 or 1;
$R_y$ is X or -L-X;
$W_1$ is phenyl or monocyclic heteroaryl, wherein each $W_1$ is optionally fused with a monocyclic, five or six-membered ring selected from the group consisting of phenyl, heteroaryl, heterocycle, cycloalkyl and cycloalkenyl; wherein each ring as represented by $W_1$ is independently unsubstituted, substituted with one, two or three $R_7$, or substituted with zero, one or two $R_7$ and one substituent selected from the group consisting of X and -L-X;
L at each occurrence is independently O, N(H), N(alkyl), S, S(O), S(O)$_2$, S(O)$_2$N(H), SO$_2$N(alkyl), N(H)S(O)$_2$, N(alkyl)S(O)$_2$, CON(H), CON(alkyl), N(H)CO, or N(alkyl)CO;
X, at each occurrence is independently aryl, heteroaryl, cycloalkyl, cycloalkenyl, or heterocycle; each of which is independently unsubstituted or substituted with one, two or three $R_7$;
$R_7$ at each occurrence is independently alkyl, alkenyl, CN, $NO_2$, halo, =O, —$OR_A$, —$SR_A$, —S(O)$R_A$, —S(O)$_2R_A$, —S(O)$_2$N($R_A$)($R_B$), —N($R_A$)($R_B$), —C(O)$R_A$, —C(O)$OR_A$, —C(O)N($R_A$)($R_B$), haloalkyl, -alkyl-$OR_A$-alkyl-$SR_A$, -alkyl-S(O)$R_A$, -alkyl-S(O)$_2R_A$, -alkyl-S(O)$_2$N($R_A$)($R_B$), -alkyl-N($R_A$)($R_B$), -alkyl-C(O)$R_A$, -alkyl-C(O)$OR_A$, or -alkyl-C(O)N($R_A$)($R_B$); and
$R_A$ and $R_B$ at each occurrence are independently hydrogen, alkyl, alkenyl or haloalkyl.

In a particular embodiment, the inhibitor is a $P2Y_6$ receptor inhibitor. Any suitable $P2Y_6$ receptor inhibitor can be used. For example, N,N''-1,4-butanediylbis[N'-3-isothiocyanatophenyl)]thiourea (or MRS 2578) can be used as a $P2Y_6$ receptor inhibitor.

Examples of other $P2Y_6$ receptor inhibitors include the diisothiocyanate derivative of 1,2-diphenylethane (MRS 2567) and 1,4-phenylendiisothiocyanate derivative MRS 2575, disclosed in Mamedova, L. K., et al., *Biochemical Pharmacology*, 67, 1763-1770 (2004).

In a particular embodiment, the inhibitor is a $P2Y_{12}$ receptor inhibitor. Any suitable $P2Y_{12}$ receptor inhibitor can be used. For example, MeSAMP can be used as a receptor inhibitor.

Examples of other $P2Y_{12}$ receptor inhibitor include anthraquinone derivatives of formula (I) disclosed in US 2010/0210654 A1.

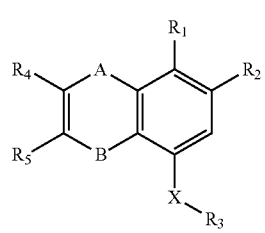

(I)

wherein:
A and B are independently $CH_2$, O, S, NH, C=O, C=NH, C=S, or C=N—OH;
X is selected from the group consisting of NH, O, S, C=O, and $CH_2$;
$R^1$ and $R^2$ are independently selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR';

$R^3$ is selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, alkylaryl, alkylheteroaryl, an unsubstituted or substituted 7 to 12-membered bicyclic alkyl or heterocyclic ring wherein 1 to 3 ring members are independently nitrogen, oxygen or sulfur, an unsubstituted or substituted 10 to 16-membered tricyclic alkyl or heterocyclic ring wherein 1 to 3 ring members are independently nitrogen, oxygen or sulfur,

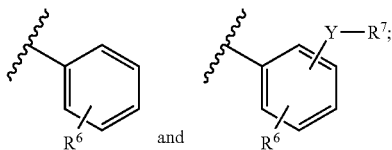

$R^4$ and $R^5$ are hydrogen, or, combined, $R^4$ and $R^5$ may, together with the carbon atoms to which they are attached, form a group selected of the groups consisting of unsubstituted or substituted $C_3$-$C_8$ cycloalkyl, unsubstituted or substituted $C_6$-$C_{14}$ aryl, unsubstituted or substituted 5- to 10-membered heteroaryl wherein 1 to 4 ring atoms are independently selected from nitrogen, oxygen or sulfur, and unsubstituted or substituted 5- to 10-membered heteroalicyclic ring wherein 1 to 3 ring atoms are independently nitrogen, oxygen or sulfur;

$R^6$ represents one to four substituents which are independently selected from the group consisting of hydrogen, halogen, unsubstituted or substituted $C_1$-$C_4$ alkyl, alkenyl or alkynyl, an unsubstituted or substituted 5- to 10-membered heteroaryl wherein 1 to 4 ring atoms are independently from nitrogen, oxygen or sulfur, an unsubstituted or substituted 5- to 10-membered heteroalicyclic ring wherein 1 to 3 ring atoms are independently nitrogen, oxygen or sulfur, —OR, —NRR', —NO$_2$, unsubstituted or substituted $C_1$-$C_4$ alkoxy, —C(O)R, —C(O)OR, —C(O)NRR', —S(O)$_2$R, —S(O)$_2$OR, and —S(O)$_2$NRR';

Y is selected from the group consisting of hydrogen, halogen, NH, O, S, CH$_2$, CH$_2$CH$_2$, C(O), C(O)O, S(O)$_2$O, or unsubstituted $C_1$-$C_4$ alkoxy, with the proviso that when Y is hydrogen, halogen or alkoxy $R^7$ is missing;

$R^7$ is selected from the group consisting of hydrogen, halogen, —OR, unsubstituted or substituted $C_1$-$C_{10}$ alkyl, alkenyl or alkynyl, unsubstituted or substituted $C_1$-$C_{10}$ alkoxy, unsubstituted or substituted $C_3$-$C_8$ cycloalkoxy, unsubstituted or substituted $C_3$-$C_8$ cycloalkyl, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic wherein 1 to 3 ring atoms are independently nitrogen, oxygen or sulfur, —C(O)R, —C(O)OR, —C(O)NRR', —NRR', —S(O)$_2$R, —S(O)$_2$OR, —S(O)$_2$NRR', and —P(O)RR'; and R and R' are independently selected from the group consisting of hydrogen and unsubstituted $C_1$-$C_4$ alkyl.

In a particular embodiment, the ROS or anti-inflammatory agent is an inhibitor of a connexin hemichannel. Any suitable connexin hemichannel receptor inhibitor can be used. For example, (3β)-3-[(3-carboxypropanoyl)oxy]-11-oxoolean-12-en-30-oic acid (or Carbenoxolone) can be used as an inhibitor of a connexin hemichannel.

Examples of other connexin hemichannel inhibitors include the antisense oligodeoxynucleotides disclosed in U.S. Pat. No. 7,098,190, for example, see col. 2, lines 1-32.

Topical administration includes direct application of the drug to the skull of the patient through the scalp. Such administration could involve rubbing the formulation onto the top of the head, providing a transdermal patch on the head, and subcutaneous injection under the scalp. For example, the hair of the patient's scalp can be removed or trimmed without injuring the skin. A portion of the topical formulation is applied to the scalp by a dropper or other applicator and the formulation allowed to penetrate the skin. A second portion and a third portion of the topical formulation can then be applied to the scalp in succession. Optionally, between each application, the scalp can be rubbed to enhance the absorption of the formulation. The rubbing can be performed manually or by an automated device such as a stroking device.

In accordance with the invention, the compounds of the invention could be directly applied to the exposed skull bone, for example, as could occur following injury or surgery. In addition, or alternatively, the compounds could be injected directly into the skull bone itself. In mammals, there are 3 layers of skull bone. The first layer is referred to as the upper cortical bone. This bone is denser than the middle layer or the cancellous bone. The cancellous bone is quite porous. Accordingly, advantageously, compounds of the invention can be administered, e.g., injected, directly into the cancellous bone. The compounds would then diffuse more quickly through the lower cortical layer of bone directly into the underlying meninges. In rodents, compounds in accordance with an embodiment of the invention applied directly to the upper cortical bone pass through all three layers. Compounds having a suitable molecular weight have the ability to pass directly through the skull. The compounds can be applied topically to the scalp; however, following injury or during surgery, compounds could be applied directly to the skull bone itself. In an embodiment, the skull bone could be removed, for example, to relieve the pressure due to severe TBI, and the compound can be administered to the injured brain.

Topically applied compositions are generally in the form of liquids, creams, pastes, lotions and gels, film, foil, paint, suspension, ointment, solution, drop, swab, infusion, or sprays. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials. In an embodiment, the therapeutic agent can be applied by subcutaneous injection under the scalp or directly into the skull bone itself.

In an embodiment, the topical formulation can be applied as a sustained release gel or transdermal patch.

Optionally, in addition to the topical administration described above, the antioxidant can also be administered to the patient via other modes of administration. Thus, multimodal administration is also contemplated within the scope of the invention so long as a topical administration is involved.

The antioxidant can be administered in combination with a pharmaceutically acceptable carrier. The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

Additionally, the antioxidants can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease or condition, for example, in a subject who is at risk for a disease such as cancer, particularly a metastatic cancer.

A typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17$^{th}$ ed., Mack Publishing Company, Easton, Pa., 1985).

It will be appreciated by one of ordinary skill in the art that, in addition to the aforedescribed pharmaceutical compositions, the anti-inflammatory agent or compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The treatment regimens can vary depending on the severity of the CNS disease or disorder. For example, particularly for treating TBI, in an embodiment, the subject is treated within at least 1 hr, within at least 2 hr, or within at least 6 hr of suffering the CNS disease or disorder. In another embodiment, the subject is treated for at least 7 days, at least 14 days, or at least 28 days after suffering the CNS disease or disorder.

The therapeutically effective amount of the compound or compounds administered can vary depending upon the desired effects and the factors noted above. In accordance with an embodiment, examples of drug dosages can be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight, per day. In embodiments, the drug dosages can be between 3 mg/kg and 85 mg/kg of the subject's body weight, or between about 3 mg/kg and 60 mg/kg, such as from about 5 mg/kg to about 60 mg/kg, from about 10 to about 60 mg/kg or from about 20 to about 60 mg/kg of the subject's body weight, per day.

Unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

The following examples further illustrate the invention but, of course, should not be construed as in any way limiting its scope.

EXAMPLE 1

Materials and Methods

Mice.

C57BL/6J (B6) and B6.129P-Cx3cr1$^{tm1Litt}$/J (CX3CR1$^{gfp/gfp}$) mice were obtained from The Jackson Laboratories. CX3CR1$^{gfp/+}$ mice were generated by crossing B6 mice with CX3CR1$^{gfp/gfp}$ mice in a close breeding facility at the National Institutes of Health (NIH). B6 LysM-GFP heterozygous knock-in mice (LysM$^{gfp/+}$) were generously provided by Dr. Thomas Graf (Albert Einstein College of Medicine) (PMID: 10887140) and maintained at the NIH. All mice were housed under specific pathogen-free conditions and treated in accordance with Institutional Animal Care and Use Committee at the NIH.

Skull Thinning & Compression Injury.

For imaging experiments, mice were anesthetized with ketamine (85 mg/kg), xylazine (13 mg/kg), and acepromazine (2 mg/kg) in PBS and maintained at a core temperature of 37° C. The skull bone over the barrel cortex was then thinned to a thickness of ~30-40 µm as described (PMID: 20134419). For this procedure, the bone was manually thinned over a 30 minute period, and the amount of downward pressure was kept to a minimum. To induce a compression injury, the skull was thinned within 5 min to a thickness of ~10-15 µm. Once thinned, the blunt of a surgical instrument was used to gently press the pliable skull bone downward. This resulted in the skull bone collapsing (without breaking)

inward toward the surface of the brain. In one set of experiments, the skull bone was intentionally cracked to induce a severe injury. Imaging was performed immediately after injury.

Intravital Two-Photon Laser Scanning Microscopy.

Mice with a normally thinned or compressed skull bone were imaged using a Leica SP5 two-photon imaging system (Leica Microsystems, Bannockburn, Ill.) equipped with an 8000 Hz resonant scanner, a 20×/1.0 NA dipping objective, and two Mai Tai HP DeepSee Lasers (SpectraPhysics) tuned to 905, 920 or 970 nm. Fluorescence emission was separated by high efficiency custom dichroic mirrors (Semrock) and collected with a NDD4 external detector (Leica). Stacks of images were acquired using a step size of 1.0 µm to a depth of 150 µm. Time lapse movies were acquired with 1 min intervals between 3D stacks. For all imaging studies, the 20× lens was submerged directly into artificial cerebral spinal fluid (aCSF; 119 mM NaCl, 26.2 mM NaHCO$_3$, 2.5 mm KCl, 1 mM NaH$_2$PO$_4$, 1.3 mM MgCl$_2$, 1.2 mM CaCl$_2$, 0.4% glucose, pH 7.4) placed atop the thinned skull.

Fluorescent Dyes.

To visualize brain vasculature, mice were injected intravenously (i.v.) 10 min prior to imaging with 50 µl Qtracker 655 nm non-targeted quantum dots in PBS (0.2 uM; Invitrogen). Cell death was visualized by incubating the thinned skull with propidium iodide (1.5 mM) in aCSF for 30 min. This was followed by a single wash with aCSF and then imaging. Reactive oxygen species (ROS) were visualized by applying Amplex Red (500 uM) transcranially for 10 min. This was followed by immediate imaging. Astrocytes were visualized by transcranially applying SR101 (10 mM) for 30 min. This was followed by a 1 hr aCSF wash and then imaging.

Purinergic Receptor, Connexin Hemichannel, and ROS Antagonism.

Prior to skull thinning, antagonists diluted in aCSF were applied directly to the skull bone, and vehicle was simultaneously applied to the opposite hemisphere to serve as a control. The following antagonists from Sigma were used: TNP-ATP hydrate (antagonist of the P2X$_4$ receptor; 25 mM), oxidated ATP (P2X$_7$; 10 mM), MRS2578 (P2Y6; diluted a 50 mM DMSO stock 1:100 in aCSF to a final concentration of 500 uM), MeSAMP (P2Y12; 10 mM), carbenoxelone (CBX) (connexin hemichannels; 100 mM), and glutathione (ROS; 100 mM). Vehicle and purinergic receptor antagonists were applied as a 3 mm diameter bubble on the skull surface and replenished as needed over a 30 min incubation period to prevent drying. This allowed the antagonists to continuously pass through the skull bone. Following the 30 min incubation, the skull was dried and then thinned to induce a compression injury over both hemispheres. Imaging was initiated immediately after injury. For most studies, the skull bone pre-incubated with antagonists was imaged continuously for 3-10 hrs, after which a 3D stack was captured from both the vehicle and antagonist treated areas for quantitative purposes. Glutathione was also applied at 15 min and 3 hrs following compression injury to determine the impact on cell death. For these studies, glutathione was added directly to the aCSF submerging solution (100 mM) while imaging. The glutathione was maintained in the submerging solution for the entire imaging experiment. A similar study was conducted using 10 mM CBX.

Glial Limitans Leakage Assay.

For permeability studies, areas of skull bone were pre-incubated with vehicle, CBX (100 mM), or glutathione (100 mM) for 30 min as described above. Afterward, a meningeal compression injury was induced. While imaging, antagonists (10 mM CBX or 100 mM glutathione) were added directly to the aCSF submerging solution. After 3 hrs of imaging, SR101 (1 mM) was applied for 15 minutes, followed by a 30 min aCSF wash. A 3D stack was then captured to quantify the degree of SR101 leakage through the glial limitans.

Skull Bone Permeability Analysis.

For skull bone permeability studies, the following rhodamine-labeled dextrans were placed directly on the intact skull bone for up to 30 min: 3,000 MW (25 mM), 10,000 MW (5 mM), 40,000 MW (1 mM), and 70,000 MW (0.5 mM). SR101 (1 mM), a sulforhodamine dye, was used as a representative of 600 MW compound. Compounds were replenished as needed to prevent drying. Following the incubation period, the skull bone was quickly thinned and imaged. A 3D stack was captured to determine if the fluorescence could be found beneath the skull bone.

Image Analysis.

All quantitative analyses and processing of 3D/4D imaging data were performed using Imaris 7.0 software (Bitplane). Supplemental movies were constructed and annotated using Adobe Premiere Pro CS4. Microglia "honeycomb" reactions were quantified from 434×434×150 µm (xyz) 3D image stacks obtained at selected time points in CX3CR1$^{gfp/+}$ mice. This was accomplished by measuring the total length of microglial processes in contact with the glial limitans. Microglial cell bodies were first selected using the Imaris "spots" tool. Afterward, 10 microglia per mouse were randomly selected for quantification of process length. Only cells with all of their processes in the field of view and no more than 50 µm beneath the skull bone were quantified. Microglial processes that were touching (flat against) the glial limitans were labeled and measured using the Imaris "filaments" tool. Data were then represented on a per cell basis as the length of microglial processes in contact with the glial limitans. Microglia with a "jellyfish" morphology were identified as those having processes greater than 20 µm in diameter. The number of "jellyfish" microglia was then divided by the total number of microglia within 50 µm of the skull bone and multiplied by 100 to generate a percentage. To quantify cell death, propidium iodide-positive cells were labeled in 3D stacks using the Imaris "spots" tool. Dead cells from 0 to 5 µm below the compressed skull were considered meningeal, whereas cells from 5 to 100 µm were considered parenchymal. The number of dead cells was divided by volume analyzed and represented as cells per mm$^3$. Neutrophils were quantified in LysM$^{GFP/+}$ mice using the Imaris "spots" tool. Following compression injury, neutrophils were never observed in the brain parenchyma, and, therefore, were quantified only in the meningeal space (0 to 5 µm below the compressed skull). The number of neutrophils was divided by the volume analyzed and represented as cells per mm$^3$. To quantify leakage of SR101 through the glial limitans, a 50×50×100 µm (xyz) solid box was generated using the Imaris "surfaces" tool. The box was placed 25 µm beneath the epicenter of the compression injury (i.e. the lowest point of the compressed skull bone). The mean fluorescent intensity of SR101 signal inside of this box was then calculated. The value obtained beneath the antagonist treated skull (glutathione or CBX) was divided by the vehicle control area (from the opposite hemisphere) to generate a fluorescence ratio.

EXAMPLE 2

This example illustrates effects of meningeal compression injury in the brain. Mice were anesthetized with ketamine, xylazine, and acepromazine. While under anesthesia, skulls were thinned surgically to a thickness of a ~15 microns and then lightly pressed downward using a blunt object until the skull bone collapsed, thereby producing a meningeal compression injury. At selected time points following compression injury, 1.5 mM propidium iodide in artificial cerebral spinal fluid (aCSF) was applied for 30 minutes transcranially. This was followed by a single wash with aCSF and then imaged intravitally. For all imaging experiments, a Leica SP5 two photon (2P) microscope fitted with two Mai Tai DeepSee lasers, a 20× (1.0 N/A) objective, a resonant scanner, and a quad external detector array, was utilized. The standard dimensions of a 3D data set were 434 μm×434 μm×100 μm (xyz) with a z step size of 1 μm. For 4D movies, z stacks were collected every 30 seconds. All data sets were analyzed using 4D image analysis software (Imaris). Dead cells were identified as being propidium iodide positive. Cells located from 0 to 5 μm below the skull bone were considered meningeal, whereas cells from 5 to 100 μm were considered parenchymal. As shown in FIG. 1, meningeal death occurred immediately after meningeal compression injury. Parenchymal death occurred 9 hours post compression injury.

EXAMPLE 3

Figure 2:
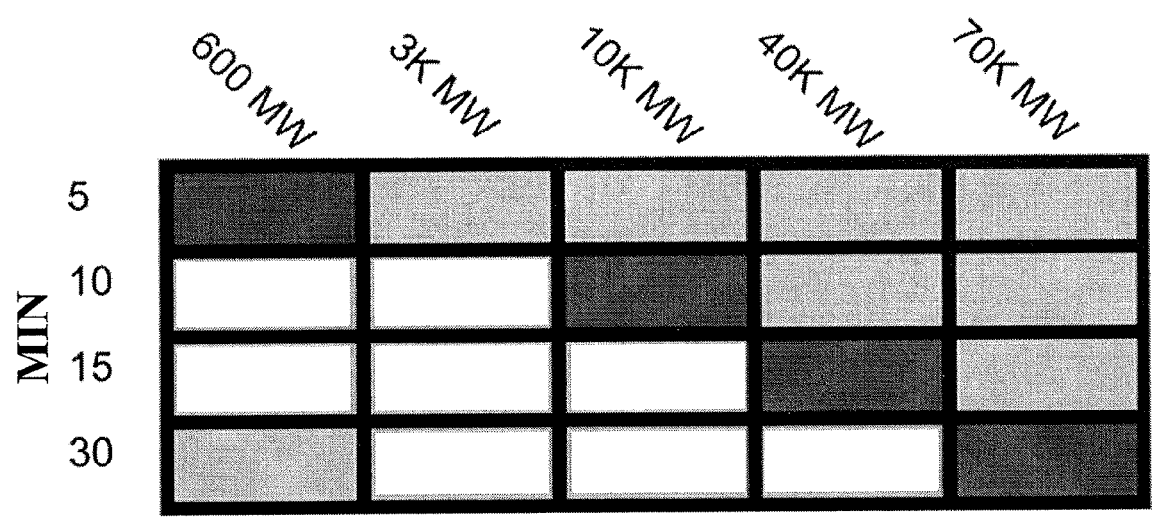

This example illustrates the effect of molecular weight of the compounds on the rate of transcranial permeation. To define the time and size of compounds that pass directly through the intact (non-thinned) skull, 10 mM SR101 (600 MW) or different sized rhodamine-dextrans (25 mM 3,000 MW; 5 mM 10,000 MW; 1 mM 40,000 MW; 0.5 mM 70,000 MW) were applied to the skull bone. A 3 mm diameter bubble was left on the skull surface for the amount of time noted in minutes on the y axis of the table above. Because all compounds fluoresced, 2P microscopy was performed immediately after transcranial loading to determine if the compounds were present in the subarachnoid space. The results obtained are shown in FIG. 2, where white indicates that a compound was found in the subarachnoid space, whereas black indicates that it was not. Gray indicates that the compound was not tested at the indicated time. Small compounds (e.g. SR101) pass through the skull more quickly than larger compounds (e.g. 40K MW dextran). 70K MW dextran was not able to pass through the skull in 30 min.

EXAMPLE 4

Figure 3:
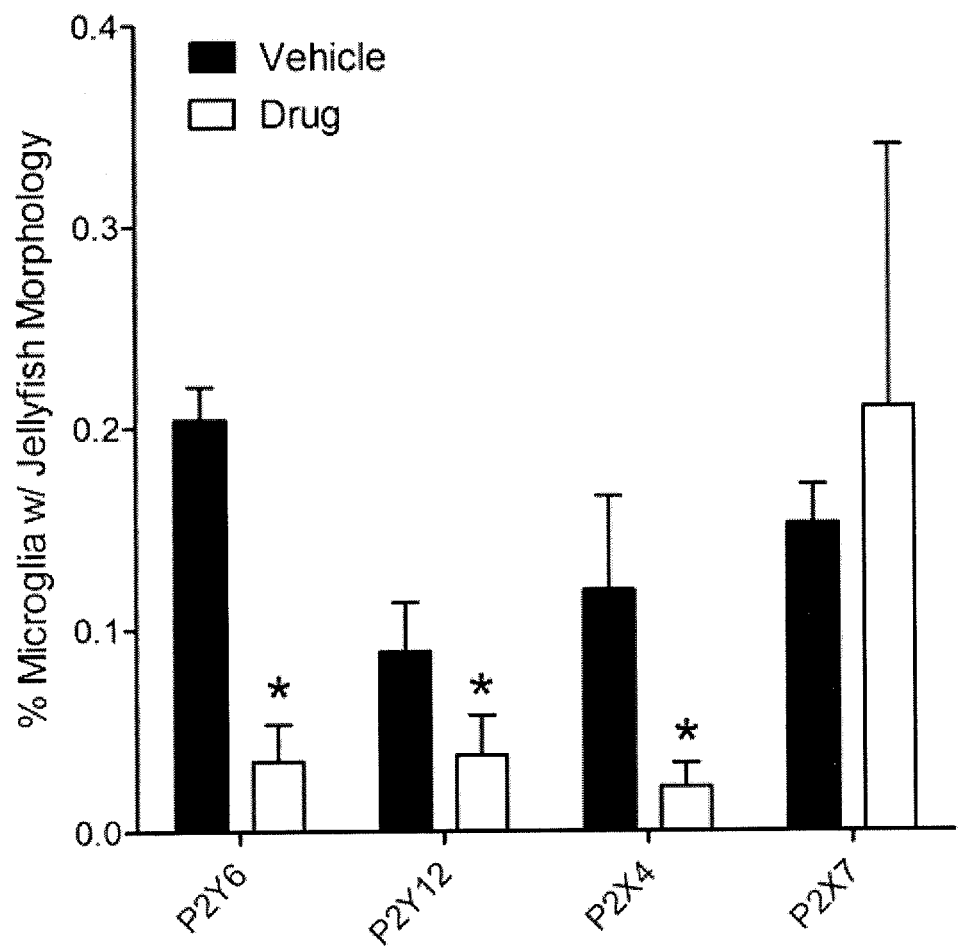

This example illustrates the effect of certain embodiment purinergic receptor antagonists in reducing the formation of phagocytic microglia when transcranially administered to the skull. The following purinergic receptor antagonists were applied directly to the skull bone in aCSF 30 min prior to inducing a meningeal compression injury: MRS2578 (500 μM; $P2Y_6$ inhibitor), MeSAMP (10 mM; $P2Y_{12}$ inhibitor), TNP-ATP hydrate (25 mM; $P2X_4$ inhibitor), and oxidized ATP (10 mM; $P2X_7$ inhibitor). aCSF was used as a vehicle control and placed on the skull bone of the opposite hemisphere. After the 30 min incubation, a meningeal compression injury was induced beneath the vehicle and drug-treated portions of skull bone. This experiment was performed in heterozygous CX3CR1-GFP mice to facilitate imaging of microglia by 2P microscopy. Phagocytic microglia with processes greater than 20 μm in diameter (referred to as the jellyfish microglia) were quantified 3 hrs post-injury. As shown in FIG. 3, transcranial administration of $P2Y_6$, $P2Y_{12}$, and $P2X_4$ (but not $P2X_7$) antagonists all significantly reduced (asterisks, $p<0.05$) the percentage of phagocytic microglia in the imaging field.

Figure 4:
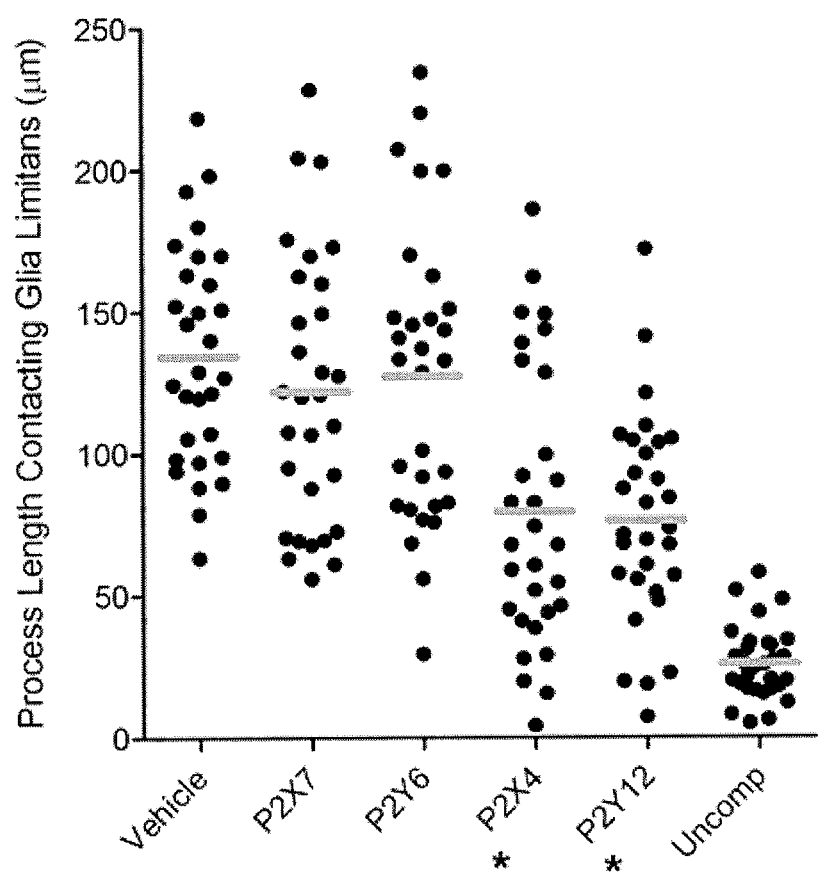
FIG. 4 depicts the process lengths of microglia extending to contact the injured glial limitans following transcranial administration of purinergic receptor antagonists to mice subjected to meningeal compression injury.

Three hours following injury, the length of microglia processes associated with the glial limitans were quantified from 2P microscopy images. Transcranial administration of $P2X_4$ and $P2Y_{12}$ (but not $P2X_7$ and $P2Y_6$) antagonists significantly reduced (asterisks, $p<0.05$) the length of microglial processes that were in contact with the glial limitans, as shown in FIG. 4.

Figure 5:
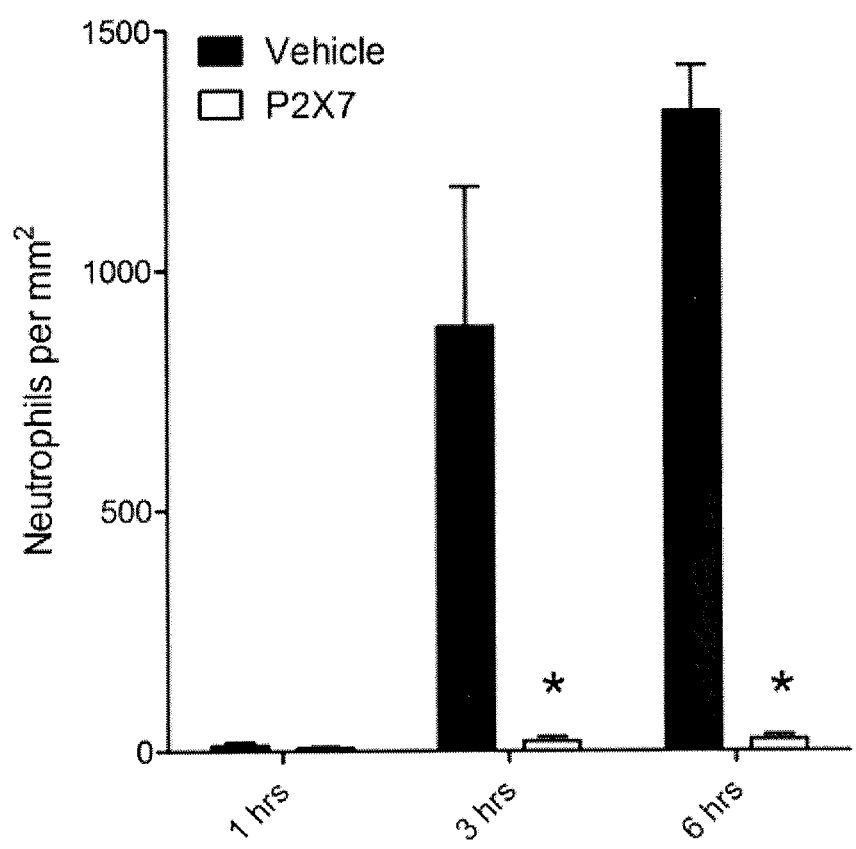
FIG. 5 depicts the number of neutrophils following transcranial administration of P2X$_7$ antagonist as a function of time in mice subjected to meningeal compression injury.

FIG. 5 illustrates that the transcranial administration of a $P2X_7$ antagonist prevents neutrophil recruitment following meningeal compression injury. A $P2X_7$ antagonist (oxidated ATP) was applied to the skull of a LysM-GFP transgenic reporter mouse as described above (see Example 4). Monocytes and neutrophils are fluorescently tagged in LysM-GFP mice and can be distinguished from one another based on their fluorescent intensity. Following meningeal compression, neutrophils are recruited to the injury site within 3 hrs. This recruitment is completely blocked (asterisks, $p<0.05$) by transcranial administration of a $P2X_7$ antagonist.

EXAMPLE 5

Figure 6:
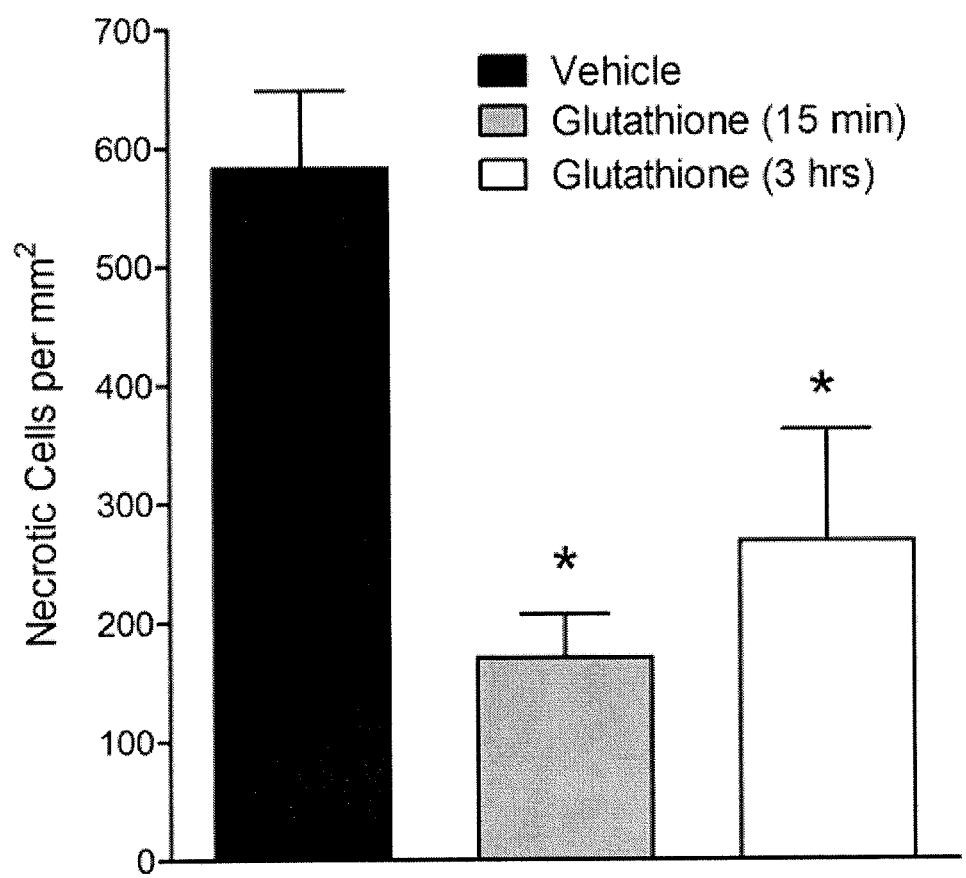
FIG. 6 depicts the ratio of the fluorescence of dye SR101 present in the parenchyma before and after pretreatment of the mice with vehicle (black bar) or glutathione (white bar), wherein the mice were subjected to meningeal compression injury.
Figure 7:
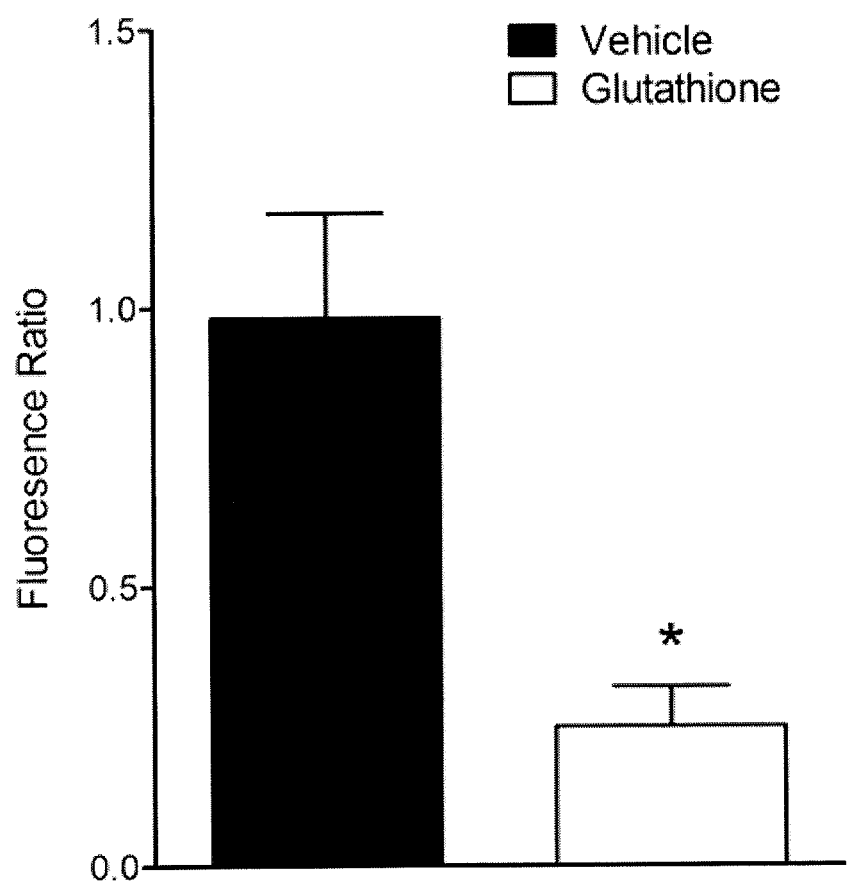
FIG. 7 depicts the number of necrotic cells in the parenchyma of mice subjected to meningeal compression injury when the mice were treated with vehicle (black bar) and glutathione (gray bar, 15 min after injury, and white bar, 3 hrs after injury).

This example illustrates the effect of glutathione in treating meningeal compression injury. As shown in FIG. 6, transcranial administration glutathione reduces the number of dead cells in the brain parenchyma. A 100 mM solution of glutathione (a reactive oxygen species scavenger) in aCSF was applied transcranially at 15 min or 3 hrs following meningeal compression and maintain until 12 hrs post-injury, at which point propidium iodide was added to label dead cells. The number of dead cells in the brain parenchyma was quantified as described in Example 2. Initiation of glutathione treatment at 15 min and 3 hrs post-injury significantly reduced (asterisks, $p<0.05$) the number of dead cells in the brain parenchyma.

EXAMPLE 6

This example illustrates that transcranial administration of glutathione reduces breakdown of glial limitans. Meningeal compression induced breakdown of the glial limitans, which is the border between the meninges and brain parenchyma. The glial limitans breakdown was quantified by administering a fluorescent dye (SR101) transcranially for 15 min (see FIG. 2). When the glial limitans membrane was intact, SR101 remains entirely in the meningeal space; however, SR101 leaked into the brain parenchyma when the glial limitans was damaged. Pretreatment with 100 mM glutathione (Example 4) significantly reduced (asterisks, $p<0.05$) the leakage of SR101 into the brain parenchyma when compared to the vehicle control group.

Figure 8:
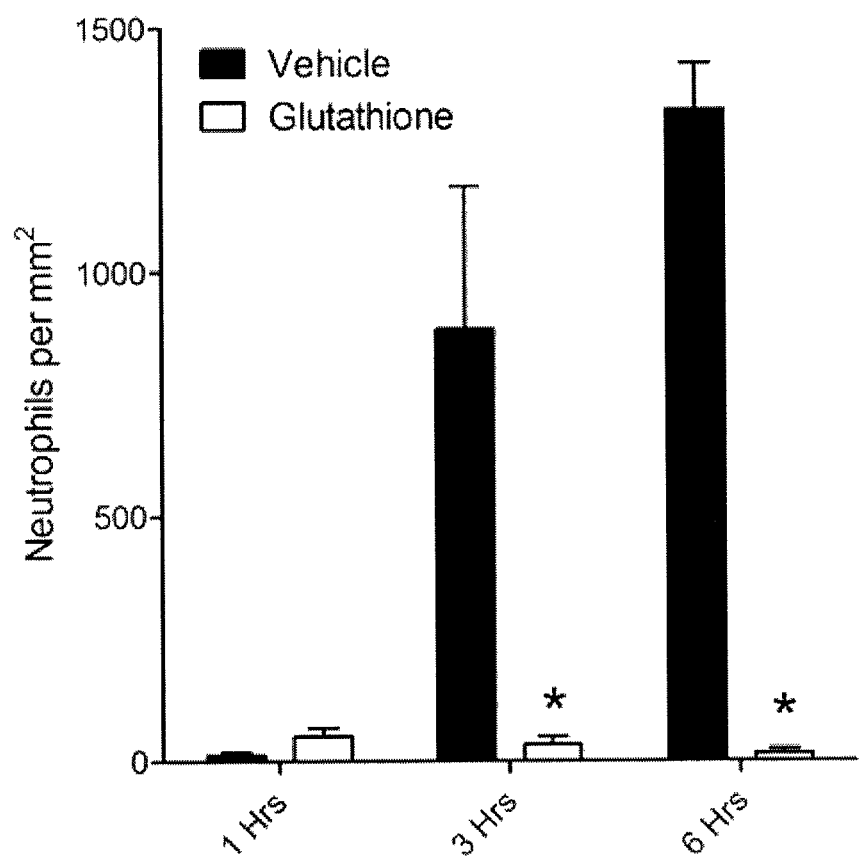
FIG. 8 depicts the number of neutrophils recruited to site of meningeal compression injury wherein the mice were pretreated by transcranial administration of vehicle (black bar) and glutathione (white bar) and then subjected to meningeal compression injury.

Further, as shown in FIG. 8, transcranial administration of glutathione limits neutrophil recruitment. As noted above (see FIG. 5), neutrophils are recruited to the site of a meningeal compression injury. Pretreatment with 100 mM glutathione (Example 4) significantly reduced (asterisks, $p<0.05$) the recruitment of neutrophils following compression injury. The reduced inflammation stems from the decrease in cellular injury (see FIG. 6).

Figure 9:
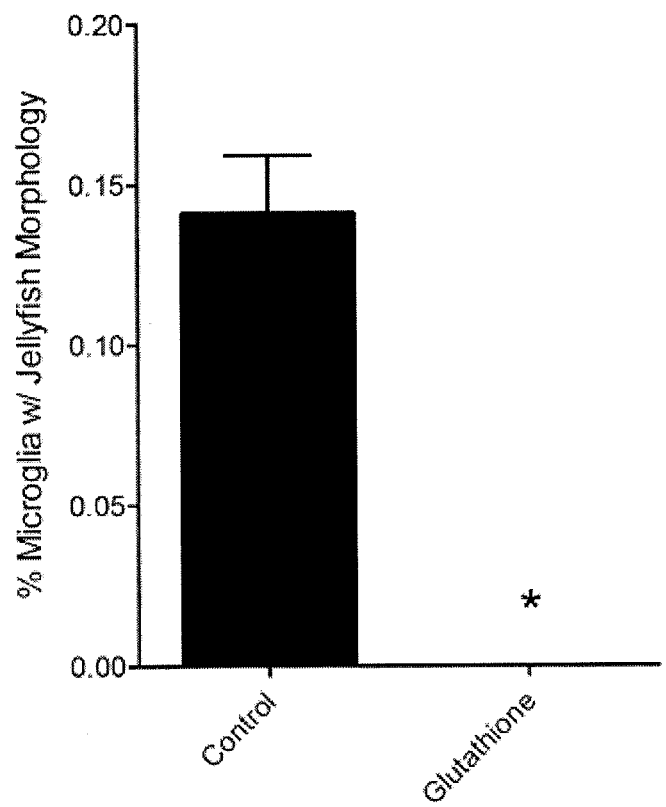
FIG. 9 depicts the percentage of microglia with jellyfish morphology present in the brain of mice subjected to meningeal compression injury, wherein the mice were pretreated with control (black bar) or glutathione (white bar).
Figure 10:
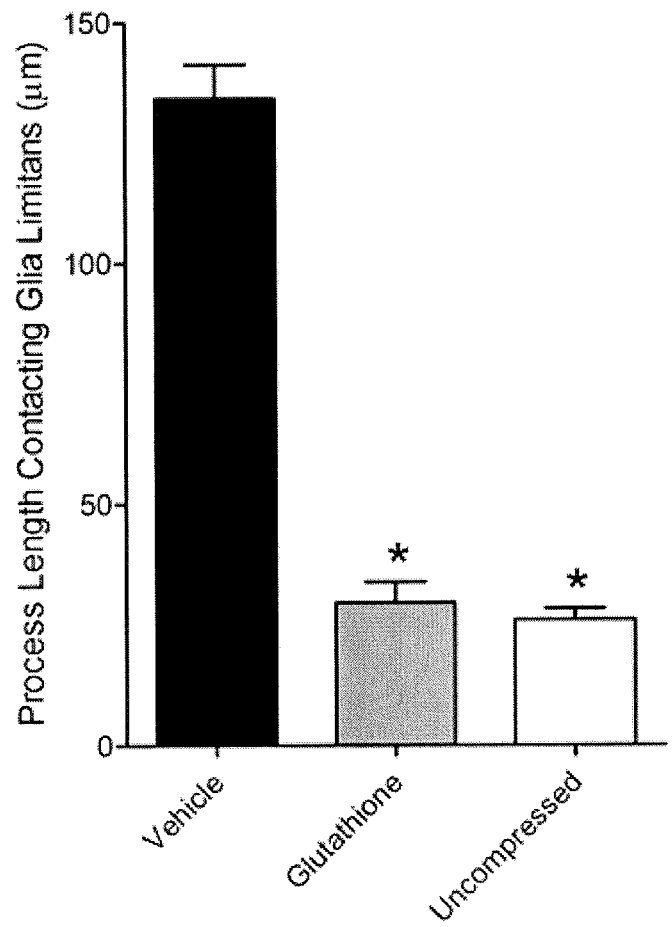
FIG. 10 depicts the process of length of microglia contacting the glial limitans in the brain of mice subjected to meningeal compression injury, wherein the mice were pretreated with vehicle (black bar) or glutathione (gray bar). The white bar represents the process length in uncompressed mice.

Furthermore, as shown in FIG. 9, transcranial administration of glutathione prevents formation of phagocytic microglia. As noted above, phagocytic microglia are generated following a meningeal compression injury. These cells participate in the cleanup of cellular debris. Pretreatment with 100 mM glutathione (as described in Example 4) eliminated the formation (asterisk, $p<0.05$) of phagocytic (jellyfish) microglia following injury. This can be explained by the fact that glutathione limits cellular damage and preserves the integrity of the glial limitans. Additionally, transcranial administration of glutathione prevents the microglia from extending their processes and contacting the glial limitans following meningeal compression injury, as shown in FIG. 10. Pretreatment with 100 mM glutathione (as described in Example 4) completely prevented this reaction.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a disease or disorder of the central nervous system (CNS) in a patient comprising administering transcranially an effective amount of an anti-inflammatory agent to the patient, wherein the anti-inflammatory agent is administered in an aqueous vehicle, and wherein the disease or disorder of the CNS is traumatic brain injury, inflammation of the brain, or stroke, wherein the anti-inflammatory agent is glutathione or a purinergic receptor inhibitor selected from trinitrophenyl-ATP hydrate, oxidized ATP, N,N"-1,4-butane-diylbis[N'-3-isothiocyanatophenyl)]thiourea, and MeSAMP, and wherein the transcranial administration comprises direct application of the anti-inflammatory agent to a skull of the patient, application of the anti-inflammatory agent to the skull through a scalp of the patient, or application of the anti-inflammatory agent into a skull bone of the patient.

2. The method of claim 1, wherein the treating comprises inhibiting, reducing, or eliminating (a) the formation of reactive microglia, (b) the recruitment of neutrophils and/or monocytes, or (c) reducing the number of dead cells in the brain parenchyma or meninges in the patient.

3. The method of claim 1, wherein the traumatic brain injury involves meningeal compression injury.

4. The method of claim 1, wherein the anti-inflammatory agent is administered via a transdermal patch.

5. The method of claim 1, wherein the anti-inflammatory agent is administered via subcutaneous injection under the scalp.

6. The method of claim 1, wherein the anti-inflammatory agent is administered via injection into the skull bone.

7. The method of claim 6, wherein the anti-inflammatory agent is administered via injection into a cancellous bone of the skull bone.

* * * * *